United States Patent [19]
Hayakawa et al.

[11] Patent Number: 6,040,439
[45] Date of Patent: Mar. 21, 2000

[54] METHOD FOR CHEMICAL SYNTHESIS OF OLIGONUCLEOTIDES

[75] Inventors: Yoshihiro Hayakawa; Masanori Kataoka, both of Aichi, Japan

[73] Assignee: Japan Science and Technology Corporation, Saitama, Japan

[21] Appl. No.: 09/145,973

[22] Filed: Sep. 3, 1998

[30] Foreign Application Priority Data

Sep. 5, 1997 [JP] Japan ........................................ 241292

[51] Int. Cl.⁷ .................................................. C07H 21/00
[52] U.S. Cl. ...................................... 536/25.34; 548/335.1
[58] Field of Search ........................ 548/335.1; 536/25.34

[56] References Cited

U.S. PATENT DOCUMENTS 5,077,285  12/1991  Claremon et al. ........................ 514/15

FOREIGN PATENT DOCUMENTS 9829429  7/1998  WIPO .

OTHER PUBLICATIONS

Arnold et al., "Chloridite and Amidite Automated Synthesis of Oligodeoxyribonucleotides Using Amidine Protected Nucleosides," reported in "7th Symposium Chem. Nucleic Acid Components," *Nucleic Acids Symposium Series*, 18, 181–184 (Aug. 30, 1987); Chemical Abstracts, 108(19), p. 692, Abstr. No. 167875z (May 9, 1988).

Hayakawa et al., "Benzimidazolium Triflate as an Efficient Promoter for Nucleotide Synthesis via the Phosphoramidite Method," *J. Organic Chemistry*, 61(23), 7996–7997 (Nov. 15, 1996).

Pirrung et al., "Proofing of Photolithographic DNA Synthesis with 3',5'-Dimethoxybenzoinyloxycarbonyl–Protected Deoxynucleoside Phosphoramidites," *J. Organic Chemistry*, 63(2), 241–246 (Jan. 23, 1998).

Effenberger et al., Trifluoromethanesulfonic Imidazolide—A Convenient Reagent for Introducing the Triflate Group, *Tetrahedron Letters*, 1980(45), 3947–3948 (Sep. 1980).

*Primary Examiner*—L. Eric Crane
*Attorney, Agent, or Firm*—Wenderoth, Lind & Ponack, L.L.P.

[57] ABSTRACT

The present invention provides a practical method capable of chemically synthesizing a 100-mer or more long-chain oligonucleotide easily and reliably and a novel compound used in said method. The present invention relates to a method for chemical synthesis of an oligonucleotide by the phosphoroamidite method, which comprises preparing a base moiety-unprotected nucleoside phosphoroamidite from a base moiety-unprotected nucleoside by use of an imidazole trifluoromethanesulfonate represented by the following chemical formula, and coupling said base moiety-unprotected nucleotide phosphoroamidite in a predetermined order to chemically synthesize an oligonucleotide consisting of a specific nucleotide sequence, as well as to an imidazole trifluoromethanesulfonate represented by the chemical formula.

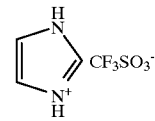

2 Claims, 3 Drawing Sheets

SEQUENCE LISTING

<160> NUMBER OF SEQ ID NOS: 1

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence: SYNTHETIC DNA

<400> SEQUENCE: 1
tatgggcctt ttgataggat gctcaccgag caaaaccaag aacaaccagg agattttatt        60

METHOD FOR CHEMICAL SYNTHESIS OF OLIGONUCLEOTIDES

BACKGROUND OF THE INVENTION

1. Field of the Invention

The present invention relates to a method for chemical synthesis of oligonucleotides. In particular, the present invention relates to a novel method capable of chemically synthesizing a long-chain DNA or RNA fragment easily and reliably from a base moiety-unprotected nucleotide phosphoroamidite as a unit, as well as to a novel compound used in said method.

2. Description of the Related Art

The phosphoroamidite method is used most widely at present as a method of chemically synthesizing oligonucleotides such as DNA fragments and RNA fragments (Nucleic Acid Research, 17:7059–7071, 1989). In general, this phosphoroamidite method makes use of a condensation reaction between a nucleoside phosphoroamidite and a nucleoside as a key reaction using tetrazole as an accelerator. Because this reaction usually occurs competitively on both the hydroxyl group in a sugar moiety and the amino group in a nucleoside base moiety, the selective reaction on only the hydroxyl group in a sugar moiety is required to synthesize a desired nucleotide. Accordingly, the side reaction on the amino group was prevented in the prior art by protecting the amino group, as illustrated in the following reaction scheme:

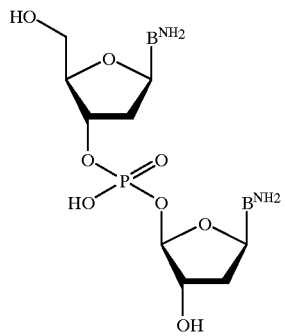

However, the protective group should be removed when synthesis was finished, and operationally complicated organic reactions and a large amount of expensive and harmful reagents are required to introduce and remove said protective group, which in view of practical usability, economical efficiency, environmental protection etc., is a great problem in carrying out this prior method. Accordingly, there is demand for a method of chemically synthesizing an oligonucleotide from an amino group-unprotected nucleoside phosphoroamidite as a unit, and the method of Letsinger et al., as shown in the following reaction scheme, is known as a pioneering method (Nucleic Acids Research, 20:1879–1882, 1992):

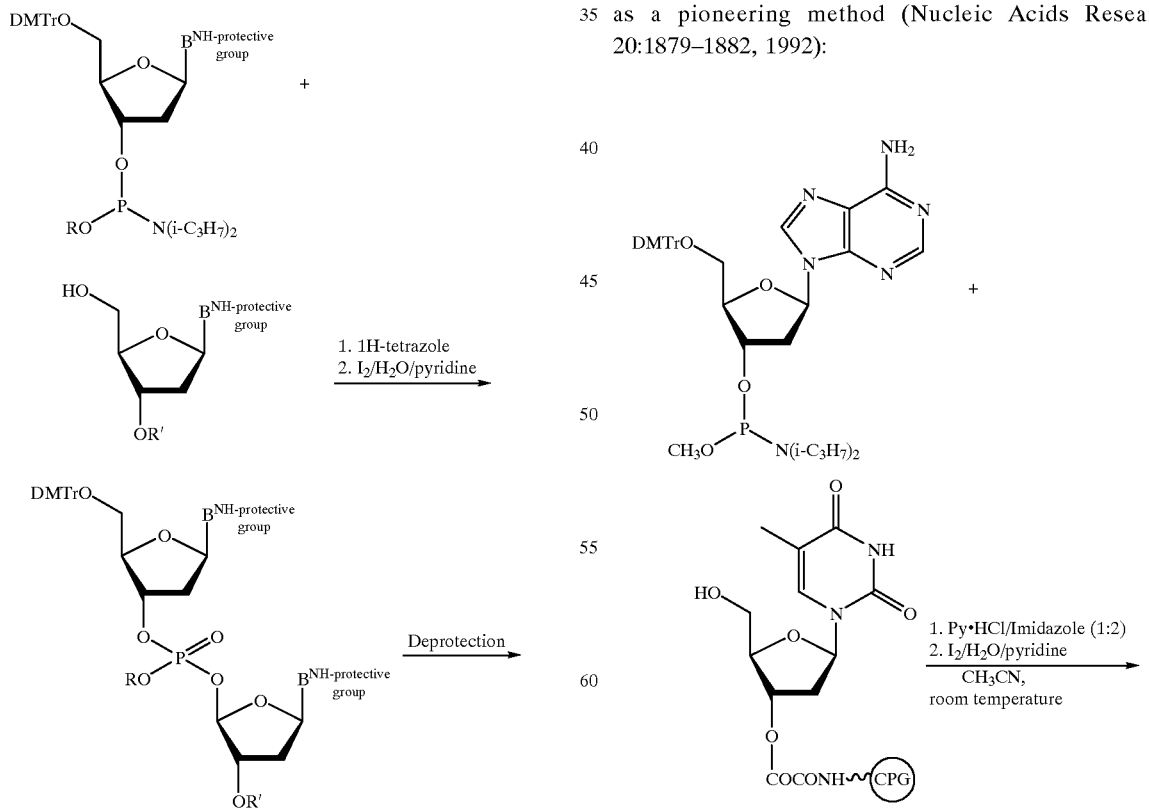

-continued

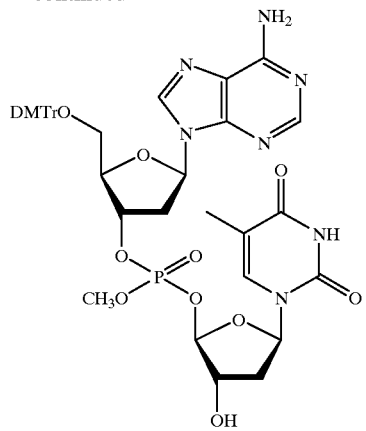

However, the method of Letsinger et al. is not practical, not universal and is not used in practice since there are following disadvantages:
(1) condensation yield in each step is low (about 97%: at least 99% yield is required for synthesis of a 50-mer or more long-chain oligonucleotide) and a commercial automatic DNA synthesizer cannot be used for this method, so a long-chain oligonucleotide consisting of 50 to 100 nucleotides generally required in chemical synthesis of DNA etc. cannot be synthesized;
(2) highly reactive, specific nucleoside phosphoroamidites only can be used, and thus this method has a limited scope of application and is not practical; and
(3) pyridine hydrochloride used as an accelerator is an unstable compound with very high moistureproofness, and thus its handling is difficult.

SUMMARY OF THE INVENTION

The present invention was made in view of the prior art described above, and the object of the present invention is to provide a practical method capable of chemically synthesizing a 100-mer or more long-chain oligonucleotide easily and reliably as well as a novel compound used in said method.

To solve the problem, the present invention provides a method for chemical synthesis of an oligonucleotide by the phosphoroamidite method, which comprises preparing a base moiety-unprotected nucleoside phosphoroamidite from a base moiety-unprotected nucleoside by use of an imidazole trifluoromethanesulfonate represented by the following chemical formula, and coupling said base moiety-unprotected nucleotide phosphoroamidite in a predetermined order to chemically synthesize an oligonucleotide consisting of a specific nucleotide sequence.

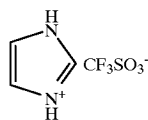

In a preferable embodiment of the method of this invention, the coupled, base moiety-unprotected nucleoside phosphoroamidite is treated with a benzimidazole trifluoromethanesulfonate solution.

Further, this invention also provides an imidazole trifluoromethanesulfonate represented by the chemical formula.

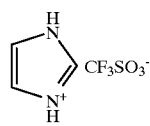

That is, the present inventors found that a base moiety-unprotected nucleoside phosphoroamidite prepared by use of a novel compound, imidazole trifluoromethanesulfonate (referred to hereinafter as imidazolium triflate) in place of the conventionally used tetrazole as an accelerator for condensation reaction between nucleoside phosphoroamidite and nucleotide is free of the side reaction on the amino group in the nucleotide base moiety thereof, and as a result, they found that complicated procedures such as, for example, introduction and removal of a protective group are not required, and also that its synthesis can be conducted by a commercial synthesizer, thereby completing this invention. Further, the present inventors found that the side reaction on the amino group in the base moiety can be completely inhibited by treating the above-described coupled, base moiety-unprotected nucleoside phosphoroamidite with a methanol solution of a benzimidazole trifluoromethanesulfonate (referred to hereinafter as benzimidazolium triflate) whereby a more perfect oligonucleotide is synthesized, and the present invention was thereby completed.

DESCRIPTION OF THE PREFERRED EMBODIMENTS

Figure 1:
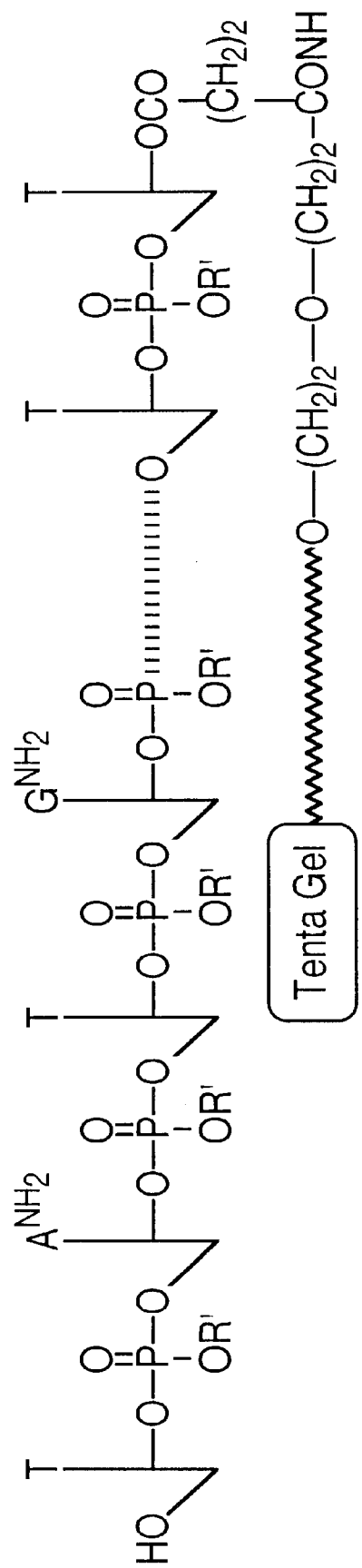
FIG. 1 is a schematic drawing of each reaction step in the method of this invention.

Hereinafter, the best mode for carrying out the present invention is described in detail.

The imidazolium triflate of the present invention can be prepared by mixing imidazole with trifluoromethanesulfonic acid in 1:1 equivalents in dichloromethane, as illustrated below in its preparation example in Example 1.

The imidazolium triflate thus obtained does not absorb moisture as also shown in Example 1 and is extremely stable under usual conditions for use, so it can be easily handled.

In the chemical synthetic method of this invention, a base moiety-unprotected nucleoside phosphoroamidite is prepared from a base moiety-unprotected nucleotide by use of the imidazolium triflate as described above, and this base moiety-unprotected nucleoside phosphoroamidite is used as a unit and each nucleoside phosphoroamidite is coupled in a predetermined order thereby chemically synthesizing an oligonucleotide consisting of a specific nucleotide sequence.

The base moiety-unprotected nucleoside phosphoroamidite can be prepared by reacting the base moiety-unprotected nucleoside phosphoroamidite with cyanoethyl-bis-amidite in the presence of the imidazolium triflate as a catalyst as illustrated e.g. in Example 2 below. In this case, the reaction occurs selectively on the hydroxide group in the sugar moiety of the nucleoside, so four kinds of N-unprotected nucleoside phosphoroamidites used in DNA synthesis, that is, deoxyadenosine, deoxythymidine, deoxyguanosine and thymidine phosphoroamidites can be obtained quantitatively.

The four kinds of N-unprotected nucleoside phosphoroamidites thus obtained are used as units to synthesize an oligonucleotide consisting of a desired nucleotide sequence by the solid-phase synthetic method etc. known in the art. Further, this synthetic reaction can also be conducted in a commercial DNA synthesizer by a method according to its protocol.

In the method of this invention, each coupled N-unprotected nucleoside phosphoroamidite is preferably subjected after each coupling to treatment with a solution (e.g. an ethanol solution) of benzimidazolium triflate. By this treatment, the side reaction on the amino group in the base moiety is completely inhibited, and a more perfect oligonucleotide is thus synthesized.

The benzimidazolium triflate can be synthesized in the following reaction scheme:

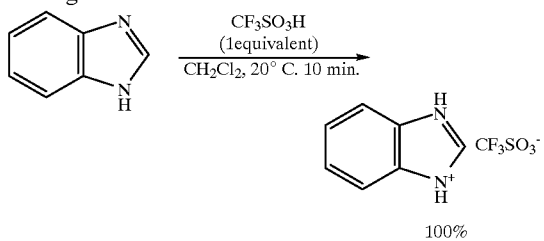

100%

EXAMPLES

Hereinafter, the present invention is described in more detail and specifically with reference to the Examples, which however are not intended to limit the present invention.

Example 1

Preparation of imidazolium triflate

Imidazole and trifluoromethanesulfonic acid were mixed in 1:1 equivalents in dichloromethane and reacted at 25° C. for 10 minutes as shown in the reaction scheme below, whereby the imidazolium triflate of this invention was prepared.

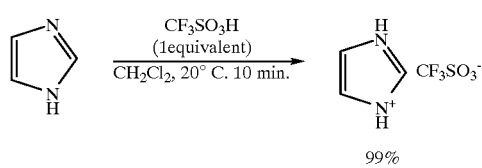

99%

As a result of analysis in conventional methods, the resulting imidazolium triflate had the characteristics shown in Table 1.

TABLE 1

Colorless crystal
Melting point: 197–198° C.
Elementary analysis
Theoretical: $C_4H_5F_3N_2O_3S$: C, 22.02; H, 2.31; N, 12.84
Found: C, 21.96; H, 2.30; N, 12.74
No moistureproofness

Example 2

Preparation of base moiety-unprotected nucleoside phosphoroamidite

The imidazolium triflate obtained in Example 1 was used as the catalyst so that a base moiety-unprotected nucleoside was reacted with cyanoethyl-bis-amidite, as shown in the following reaction scheme:

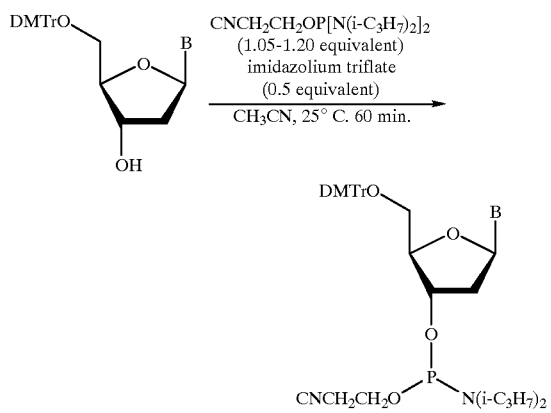

By this reaction, the four kinds of N-unprotected nucleoside phosphoroamidites shown in Table 2, that is, deoxyadenosine, deoxythymidine, deoxyguanosine and thymidine phosphoroamidites were prepared respectively. As also shown in Table 2, the respective nucleoside phosphoroamidites were obtained almost quantitatively.

TABLE 2

| B | ![adenine] | ![cytosine] | ![guanine] | ![thymine] |
|---|---|---|---|---|
| yield, %: | 96 | 98 | 97 | 99 |
| purity, %: | >98 | >98 | >96 | >99 |
| $^{31}$P NMR, ppm: | 149.0, 149.1 | 149.2, 149.3 | 149.1, 149.2 | 149.0, 149.1 |

Example 3

Synthesis of DNA fragment

From the 4 kinds of N-unprotected nucleoside phosphoroamidites as units obtained in Example 3 [sic.], a 60-mer DNA fragment consisting of the nucleotide sequence of SEQ ID NO: 1 was synthesized by the solid-phase synthetic method using a commercial DNA synthesizer. The reaction cycle was as shown in Table 3.

TABLE 3

| Step | Operation | reagent(s) | time, min |
|---|---|---|---|
| 1 | washing | $CH_3CN$ | 0.50 |
| 2 | ditritylation | 3% $CCl_3COOH/CH_2CH_2$ | 1.0 × 3 |
| 3 | washing | $CH_3CN$ | 2.0 |
| 4 | coupling | 0.1M amidite/$CH_3CN$ + 0.1M IMT/$CH_3CN$ | 0.25 |
| 5 | wait | | 1.0 |
| 6 | N-P cleavage | 0.3M BIT/$CH_3CN$ | 0.50 |
| 7 | wait | | 2.0 |
| 8 | washing | $CH_3CN$ | 0.50 |
| 9 | oxidation | 1M t-$C_4H_9OOH/CH_2Cl_2$ | 0.25 |
| 10 | wait | | 1.0 |

BIT = benzimidazolium triflate;
IMT = imidazolium triflate

In this synthetic reaction, each step (condensation reaction) in the chain-elongation shown in Table 1 proceeded in almost 100% yield, and a phosphate moiety-protected 60-mer oligonucleotide was obtained usually in 100% yield. This yield was extremely high in considering that the yield of a 60-mer oligonucleotide by generally conducted conventional methods is about 20 to 40%.

Figure 2:
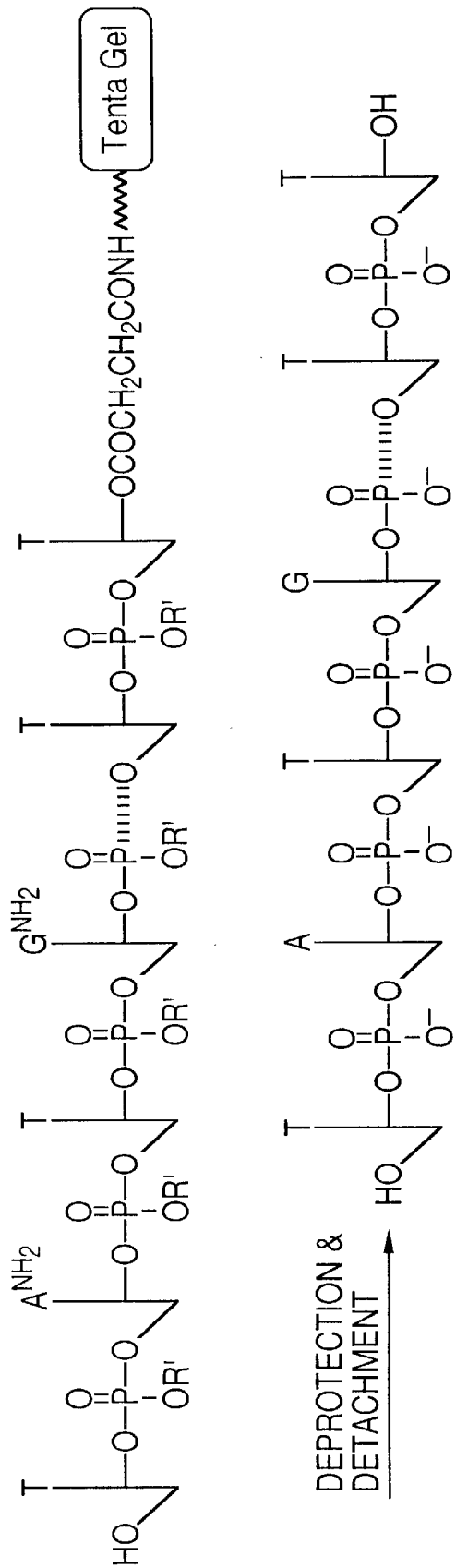
FIG. 2 is a schematic drawing of each reaction step in the method of the present invention where ammonia treatment was performed.

Further, as shown in FIG. 2, deprotection and elimination by treatment with an ammonia solution (25° C., 60 minutes) were carried out whereby the unprotected 60-mer DNA was obtained in quantitative yield.

Figure 3:
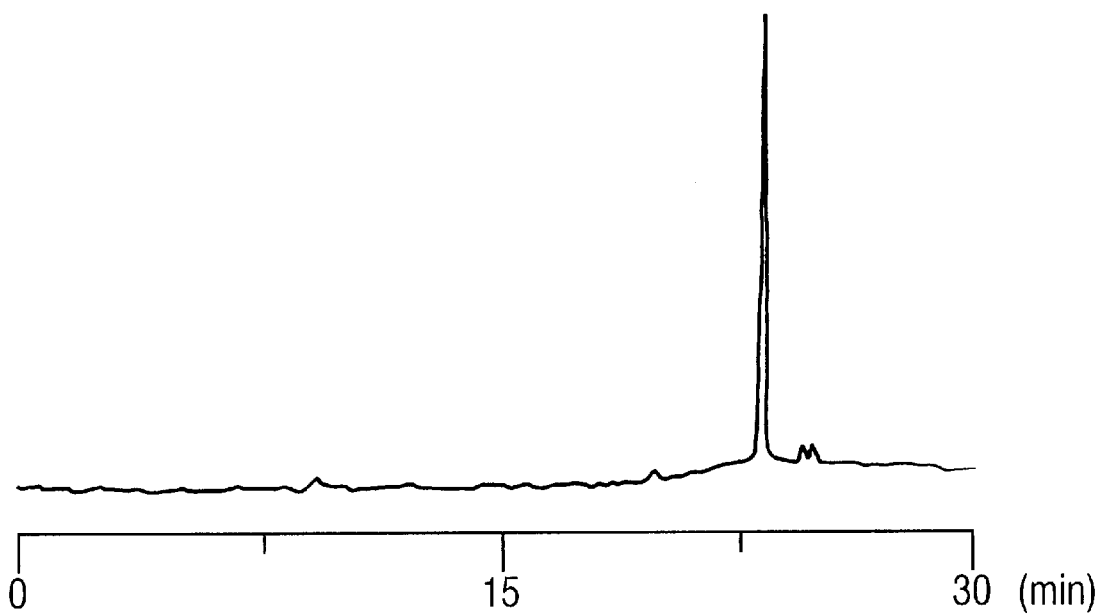
FIG. 3 is a HPLC profile of DNA fragments synthesized in the method of this invention.

Analysis of the resulting crude unprotected 60-mer DNA by high performance liquid chromatography under the conditions shown in Table 4 indicated that its purity was 95% or more as shown in FIG. 3.

TABLE 4

| Analytical conditions | |
|---|---|
| Column: | DEAE-2.5μ (250 mm) |
| Flow rate: | 0.5 mL/min |
| Temperature: | 25° C. |

TABLE 4-continued

| Analytical conditions | |
|---|---|
| Eluent: | |
| A: | 20 mM Tris-HCl (pH 9.0) |
| B: | A + 1M NaCl |
| Gradient: | A:B (100:0) → (50:50) linear gradient |

As described above in detail, the imidazolium triflate that is the novel compound of this invention and the method of synthesizing oligonucleotides by use of this imidazolium triflate have the following advantages:

(1) condensation yield in each step is as high as 100%, and the present method can also be applied to an automatic synthesizer by merely changing a program for synthesis and reagents used, so synthesis of a long-chain oligonucleotide consisting of 50 to 100 nucleotides generally required in chemical synthesis of DNA etc. is feasible in 1/10 or less costs as compared with those of conventional methods;

(2) because unspecified nucleotide phosphoroamidites can be used, the present method has a broad scope of application and is practical; and (3) the imidazolium triflate of this invention used as an accelerator is a stable compound which does not absorb moisture, so its handling under usually conditions for use is very easy.

What is claimed is:

1. A method for chemically synthesizing an oligonucleotide by a phosphoroamidite method, which comprises:

reacting amino group-unprotected nucleosides individually with a phosphoroamidite reagent in the presence of imidazole trifluoromethanesulfonate represented by the following chemical formula:

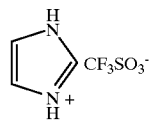

to prepare amino group-unprotected nucleoside phosphoroamidites; and coupling each of the prepared amino group-unprotected nucleoside phosphoroamidites in a predetermined order to chemically synthesize the oligonucleotide of a specific nucleotide sequence.

2. The method according to claim 1, wherein the coupled amino group-unprotected nucleoside phosphoroamidite is treated with a benzimidazole trifluoromethanesulfonate solution.

* * * * *